(12) United States Patent
Kruse et al.

(10) Patent No.: US 9,375,514 B2
(45) Date of Patent: Jun. 28, 2016

(54) MULTICELLULAR TISSUE AND ORGAN CULTURE SYSTEMS

(75) Inventors: Charli Kruse, Herrnburg (DE); Gunter Fuhr, Berlin (DE)

(73) Assignee: FRAUNHOFER-GESELLSCHAFT ZUR FORDERUNG DER ANGEWANDTEN FORSCHUNG E.V., Munich (DE)

( * ) Notice: Subject to any disclaimer, the term of this patent is extended or adjusted under 35 U.S.C. 154(b) by 1738 days.

(21) Appl. No.: 11/597,317

(22) PCT Filed: May 9, 2005

(86) PCT No.: PCT/EP2005/004996
§ 371 (c)(1),
(2), (4) Date: Feb. 4, 2008

(87) PCT Pub. No.: WO2005/113747
PCT Pub. Date: Dec. 1, 2005

(65) Prior Publication Data
US 2008/0193421 A1 Aug. 14, 2008

(30) Foreign Application Priority Data
May 21, 2004 (DE) .......................... 10 2004 025 081

(51) Int. Cl.
C12N 5/00 (2006.01)
A61L 27/38 (2006.01)
A61K 35/12 (2015.01)

(52) U.S. Cl.
CPC .......... *A61L 27/3886* (2013.01); *A61L 27/3839* (2013.01); *C12N 5/0062* (2013.01); *A61K 35/12* (2013.01)

(58) Field of Classification Search
CPC ............................ A61K 35/12; C12N 5/0633
See application file for complete search history.

(56) References Cited

FOREIGN PATENT DOCUMENTS

| | | |
|---|---|---|
| DE | 103 07 487 | 9/2004 |
| WO | WO 00/78929 | 12/2000 |
| WO | WO 03/029446 | 4/2003 |
| WO | WO 2004/029230 | 4/2004 |
| WO | WO 2005/001072 | 1/2005 |
| WO | WO 2005/026392 | 3/2005 |
| WO | WO 2005/097975 | 10/2005 |

OTHER PUBLICATIONS

Zulewski et al. (2001, Diabetes 50: 521-533).*
Otonkoski et al (J Clin Invest, 92: 1459-1466, 1993).*
Lardon et al (Hepatology, 39: 1499-1507, published on line May 27, 2004).*
Reubinoff et al (Nature Biotechnology, 19: 1134-1140, 2001).*
Theise (Stem cell Reviews 2005;1:9-13).*
Djuric et al (Stem Cell Research & Therapy 2010, 1: 1-6).*
Serafini and Verfaillie (Semi Reprod Med 2006; 24: 379-88).*
Geraerts and Verfaillie (Adv Biochem Eng Biotechnol 2009; 114:1-21).*
Preeti Gokal Kochar (Overview, pp. 1-12, 2004).*
Ulloa-Montoya et al (Journal of Bioscience and Bioengineering, 100(1): 12-27, 2005).*
Animals (Verfaillie, et al (Trends in Cell Biology, 12(11): 502-508, 2002.*
Fraker et al (Stem Cells, 25: 3155-3164, 2007).*
Conley et al., "Derivation, Propagation and Differentiation of Human Embryonic Stem Cells", The International Journal of Biochemistry & Cell Biology, 36, 2004, pp. 555-567.
Itskovitz-Eldor et al., "Differentiation of Human Embryonic Stem Cells into Embryoid Bodies Comprising the Three Embryonic Germ Layers", Molecular Medicine, vol. 6, No. 2, Feb. 2000, pp. 88-95.
Yamada et al., "In Vitro Functional Gut-Like Organ Formation from Mouse Embryonic Stem Cells", Stem Cells 2002; 20:41-49.
Ramiya et al., "Reversal of Insulin-Dependent Diabetes using Islets Generated In Vitro from Pancreatic Stem Cells", Nature Medicine, vol. 6, No. 3, Mar. 2000, pp. 278-282.
Tokoro et al., "Differentiation of Acinar Cells into Acinoductular Cells in Regenerating Rat Pancreas", Pancreatology: Official Journal of the Intern. Association of Pancreatology, vol. 3, No. 6, 2003, pp. 487-496.
Weissman et al., "Stem and Progenitor Cells: Origins, Phenotypes, Lineage Commitments, and Transdifferentiations", Annual Review of Cell and Developmental Biology, 2001, vol. 17, 2001, pp. 387-403.
Kruse et al., "Pluripotency of Adult Stem Cells Derived from Human and Rat Pancreas", Applied Physics A: Materials Science & Processing, vol. 79, No. 7, Nov. 2004, pp. 1617-1624.
Anderson et al., "The Human Plasma Proteome, History, Character, and Diagnostic Prospects", Molecular & Cellular Proteomics, ASBBM, Birmingham, vol. 1, No. 11, 2002, pp. 845-867.
Lakshmanan, "Nerve Growth Factor Levels in Mouse Serum: Variations Due to Stress", Neurochemical Research, vol. 12, No. 4, 1987, pp. 393-397.
Tai et al., "Role of Pancreatic Stem Cells in the Emergence of Pancreatic Stellate Cells and Fibroblast-Like Cells in Chronic Pancreatitis", vol. 27, No. 4, Nov. 2003, pp. 413-414.
Wobus et al., "Specific Effects of Nerve Growth Factor on the Differentiation Pattern of Mouse Embryonic Stem Cells In Vitro", Biomed. Biochim. Acta 47, 1988, pp. 965-973.
International Search Report for PCT International Application No. PCT/EP2005/004996 mailed Feb. 21, 2006.
Bachem et al., "Identification, Culture, and Characterization of Pancreatic Stellate Cells in Rats and Humans", Gastroenterology, 115:421-432 (1998).
Grosfils at al., Res. Comm. Chem. Pathol. Pharmacol. 79:99-115 (1993).
Wiese et al., 'Nestin Expression—A Property of Multi-lineage Progenitor Cells?', Cellular and Molecular Life Sciences, Oct. 2004; 61(19-20):2510-22, Baltimore, Maryland.

* cited by examiner

*Primary Examiner* — Deborah Crouch
*Assistant Examiner* — Magdalene Sgagias
(74) *Attorney, Agent, or Firm* — Pearl Cohen Zedek Latzer Baratz LLP

(57) ABSTRACT

The invention relates to methods for producing three-dimensional multicellular tissue and organ culture systems using multicellular mammalian cell aggregates, these systems themselves and their use for various medical purposes, in particular implantations.

19 Claims, 6 Drawing Sheets

200 µm         200 µm

MULTICELLULAR TISSUE AND ORGAN CULTURE SYSTEMS

PRIOR APPLICATION DATA

The present application is a National Phase Application of PCT International Application No. PCT/EP2005/004996, entitled "Multicellular Tissue And Organ Culture Systems", International Filing Date May 9, 2005, published on Dec. 1, 2005 as International Publication No. WO 2005/113747, which in turn claims priority from German Patent Application No. DE 10 2004 025 081.2, filed May 21, 2004, both of which are incorporated herein by reference in their entirety.

FIELD OF THE INVENTION

The invention relates to methods for the production of multicellular tissue and organ culture systems, these systems themselves and their use for various medical purposes, particularly implantations.

BACKGROUND OF THE INVENTION

In order to restore or assume the function of a damaged or lacking tissue or organ the transplantation of natural tissues or organs from another donor or, if possible, the concerned individual himself is an established practice that has long been known. Due to the constant lack of suitable donor tissues and donor organs and other disadvantages of natural tissue, e.g., rejection reactions and the risk of the transfer of diseases from the donor to the recipient, many efforts are being directed to the production of artificial tissues and organs as alternatives.

A customary procedure for this is the provision of a carrier or matrix structure from material compatible with the body that is colonized with differentiated cells of the target tissue, and the cultivation of the cells in vitro until a tissue-like cell structure has been produced. The differentiated cells are obtained either from cultures of explanted tissue samples or from stem cells that had been stimulated to differentiate. The use of stem cells permits a more rapid production of larger amounts of the desired cells in many instances. Traditionally, pure cell populations of a certain type are produced. Most of the in vitro organs or in vitro tissues known in the state of the art are disadvantageous in as far as that they do not have or do not develop the tissue structure that corresponds to the morphological constitution of the native tissue or organ even after implantation and a fairly long residence time in the body. This applies as a rule even when the carrier matrix had been colonized with several different populations of tissue-typical cells.

Another approach for treating degenerative diseases or damage to tissues and organs using stem cells consists in implanting the stem cells and/or differentiated cells derived from them directly into the damaged tissue/organ in order to proliferate there and result in a regeneration of the damaged tissue/organ. In this instance too the implantation or regeneration of a certain cell type traditionally is in the foreground. The problem is, however, that in very many degeneration phenomena or damages to various organs a plurality of cells is always involved so that, e.g., in the skin keratinocytes, epithelial cells and blood vessels are also affected in addition to fibroblasts. In the case of nerve damage even glia cells often have to be replaced too and muscle damage often means destruction of the accompanying nerves.

SUMMARY

Accordingly, one object of the invention is to provide improved multicellular tissue and organ culture systems, in particular human systems, that are constituted of several different cell types and comprise natural tissue and/or organ structures or that have the potential to develop them. A related object is the provision of treatment methods using these tissue and organ culture systems for restoring or assuming the function of damaged or lacking organs inside or outside the damaged body.

The present invention is based on the finding that multipotent or pluripotent adult stem cells like those that can be obtained from exocrine glandular tissue (PCT 2004/003810) can be made to aggregate and differentiate into three-dimensional cell aggregates, so-called organoid bodies, with simple means which organoid bodies already contain a spectrum of different cell types without the addition of special differentiation factors. The organoid bodies constantly continue to grow, if supplied with sufficient nutrients, and develop tissue-like or organ-like structures. They are also referred to in this stage as tissue bodies. On account of their multicellular constitution and the already present tendency to form tissue-like and organ-like structures, these organoid bodies are the ideal starting material for producing multicellular tissue and organ culture systems whose structure largely corresponds to that of native tissues or organs or that result in the formation of such native structures in the body.

Thus, the above-cited objects are achieved in accordance with the invention with the methods for producing multicellular tissue and organ culture systems in accordance with Claims 1-21, the tissue and organ culture systems in accordance with Claim 22 as well as the usages of these tissue and organ culture systems for restoring or assuming the function of damaged or lacking organs in accordance with Claims 23-27 and their use for producing tissue-specific or organ-specific substances in accordance with Claim 28.

In order to form the organoid bodies used in accordance with the invention, multipotent or pluripotent adult stem cells are used. These pluripotent stem cells are preferably isolated from exocrine glandular tissue.

The exocrine glandular tissue can stem from an adult individual or juvenile individual. The concept "adult" as used in the present application thus refers to the development stage of the starting tissue and not to that of the donor from which the tissue stems. "Adult" stem cells are non-embryonic stem cells.

The exocrine glandular tissue is preferably isolated from a salivary gland, lachrymal gland, sebaceous gland, sweat gland, from glands of the genital tract including the prostate, or from gastrointestinal tissue, including the pancreas, or from secretory tissue of the liver. A highly preferred embodiment concerns acinar tissue. The acinar tissue stems especially preferably from the pancreas, the parotid gland or the mandibular salivary gland.

The adult stem cells obtained from such sources can be readily isolated and maintained in a stable long-time culture without a feeder cell layer or special additives in a largely undifferentiated state. The concept feeder cells, as used here, comprises all cells that promote the growth of the cells to be actually cultivated in that they release growth factors and/or provide an extracellular matrix and/or prevent the differentiation of the stem cell culture.

These adult stem cells can be stimulated in a simple manner to differentiate without the addition of special growth factors or differentiation factors in that they are cultivated under spatial conditions that ensure a three-dimensional contact of the cells. In a preferred embodiment these conditions are the cultivation in hanging drops such as has already been described for embryonic stem cells (Wobus et al., Biomed. Biochim. Acta 47:965-973 (1998). This method will be described in more detail below in the examples. It is understood, however, that alternative cultivating methods that ensure the desired three-dimensional contact of the cells and are known and available to those skilled in the art can also be used. Examples of such alternative methods are the cultivation in a moved suspension culture, the cultivation in an electromagnetic field cage or laser tweezer, the spreading of non-re-suspended cells of the primary culture, or the cultivation on surfaces to which the cells do not adhere or adhere only poorly. Such surfaces may be, e.g., glass, polystyrene or surfaces treated with an anti-adhesion layer, e.g., surfaces coated with PTFE or poly-HEMA.

Under these conditions three-dimensional cell compounds or cell aggregates spontaneously develop that have been referred to as "organoid bodies" in analogy with "embroid bodies" already described for embryonic stem cells. These organoid bodies can be transferred into suspension cultures or adhesion cultures and further cultivated. Given a sufficient supply of nutrients, these organoid bodies continue to grow and can achieve diameters of a few millimeters or more. These large organoid bodies exhibit a tissue-like structure and are also referred to in this stage as "tissue bodies" in order to distinguish them from the simple cell aggregates.

If the organoid bodies are brought back into surface culture a cellular monolayer is produced from outgrowing individual cells from which monolayer multi-layer areas arise from which secondary organoid bodies are spontaneously formed with comparable properties as those of the primary organoid bodies. The organoid bodies in accordance with the invention can be stored frozen, e.g., at the temperature of liquid nitrogen, without losing their viability and their ability to reproduce, grow and differentiate.

The organoid bodies contain different cell types of all three germ layers. Differentiated cells that may be contained in the organoid bodies comprise bone cells (osteoblasts and osteoclasts), chondrocytes, adipocytes, fibroblasts (e.g., skin- and tendon fibroblasts), muscle cells, endothelial cells, epithelial cells, hematopoietic cells, sensory cells, endocrine and exocrine glandular cells, glia cells, neuronal cells, oligodendrocytes, blood cells, intestinal cells, cardiac cells, lung cells, liver cells, kidney cells or pancreatic cells but are not limited to them.

The different differentiated cell types can be identified and characterized by histological, immunocytochemical and electronic microscope techniques.

The presence of a certain cell type can be determined, e.g., using the specific morphology of this cell type or via the detection of cell-type-specific marker substances. A few cell-type-specific examples of marker substances are mentioned in the following but are in no way to be considered as limiting: PGP 9.5 and NF for nerve cells, S 100 and GFAP for glia cells, SMA for muscle cells (and myofibroblasts), type II collagen for cartilage cells, amylase and trypsin for exocrine glandular cells, insulin for endocrine glandular cells, vigilin for strongly translating cells and cytokeratin for epidermal cells, type II collagen for chondrocytes, osteonectin for osteoblasts and precursor cells, osteocalcin for mature osteoblasts, CD45, CD34, CD13 for hematopoietic cells, cTNI (cardiac troponin I), cTNT (cardiac troponin T) and ANF (atrial natriuretic factor) for cardiomyocytes, collagenase 1 and TIMP-1 (tissue inhibitor of metalloproteinase I) for fibroblasts, skeletal alpha actin and tropomyosin for striated muscle cells, lipoprotein lipase (LPL) for adipocytes, alpha fetoprotein for liver cells. A very large number of such marker substances is known in the state of the art.

These markers substances can be detected, e.g., by binding to a specific binding partner that is conjugated with a detectable group. The detectable group may be, e.g., a dye, fluorescent dye, a radioactive marking, enzyme marking, luminescence marking, magnetic resonance marking or another marking known in the state of the art. If the marker substance is a protein the binding partner will preferably be a marked or markable antibody. Such marked antibodies are already known for a plurality of marker substances and can either be acquired in trade or readily produced according to known methods. Optionally, marked or markable secondary antibodies may also be used. A few typical protein markers for e.g., nerve cells and glia cells, muscle cells and secretory cells as well as immunohistochemical detection methods for them are described in the example section.

Although basically no external differentiation factors are necessary for the differentiation of the stem cells, such differentiation factors may be used with advantage in order to produce purposefully larger amounts of a certain cell type and/or in order to generate organoid bodies with a certain cell type composition.

Differentiation factors and/or growth factors are known in the state of the art and comprise, e.g., bFGF (basic fibroblast growth factor) for an increased formation of cardiac cells and fibroblasts, VEGF (vascular endothelial growth factor), DMSO and isoproterenol, fibroblast growth factor 4 (FGF4), hepatocyte growth factor (HGF) for an increased formation of cardiac and liver cells, TGF beta1 (transforming growth factor beta1) for an increased formation of cardiac cells, EGF (epidermal growth factor) for an increased formation of skin cells and cardiac cells, KGF (keratinocyte growth factor) (sometimes together with cortisone) for the formation of keratinocytes, retinoic acid for an increased formation of nerve cells, cardiac cells and kidney cells, beta-NGF (beta nerve growth factor) for an increased formation of brain cells, liver cells, pancreatic cells and kidney cells, BMP-4 (bone morphogenic protein 4) and activin-A for the formation of mesodermal cells, but are not limited to them. In view of the extensive literature on this topic (see, e.g.: "*Adult Stem Cells*", editor K. Turksen, Human Press, 2004) those skilled in the art will be readily able to identify and, if necessary, to use other suitable factors depending on the type of cells and/or cell combinations.

The particular suitable differentiation factors and/or growth factors can be present in a substantially pure form dissolved or immobilized in the culture medium. When using immobilized differentiation factors they are preferably located on a movable carrier that can be positioned relative to the stem cells or to the organoid bodies. This can advantageously achieve a purposeful differentiation of individual cells or cell groups. The carrier is, e.g., a suitable synthetic substrate or a biological cell or cell membrane on whose surface the differentiation factors are located.

Alternatively, supernatants of cell or tissue cultures that contain the desired differentiation factors and/or growth factors can also be added to the culture medium, or the organoid bodies or stem cells can be co-cultivated with suitable differentiated cells or tissues that produce these differentiation factors and/or growth factors. Optionally, a cryo-preservation of this co-cultivated mixture may also be advantageous.

Yet another possibility is the activation or stimulation of at least one gene that is involved in the differentiation of the stem cells to the desired differentiated cells so that the latter form the necessary differentiation factors themselves to an increased degree.

In an advanced stage of the differentiation the organoid bodies have structures that are similar to tissue or organs formed from two or more different cell types (cf. FIG. 2-6).

Such structures are, e.g., neuromuscular structures (FIG. 5) or glia nerve cell structures (FIG. 6) or skin cell structures. The formation of desired structures can be promoted by cultivation of the organoid bodies in a medium with special differentiation factors.

In a preferred embodiment the differentiation factors and/or growth factors are immobilized on a movable carrier as described above and specifically the cell groups that have these structures are supplied with the necessary factors.

In another preferred embodiment the structures that are similar to tissues or organs are removed from the organoid bodies and then cultivated further under suitable conditions for maintaining and/or developing the structures, including the supplying with the suitable differentiation and growth factors in one of the above-described manners until a desired cell amount and/or a desired development stage has been attained. The removal can take place, e.g., with the aid of slow micromanipulation techniques such as are described, e.g., in DE 103 07 4B7.2.

There are basically several procedures for producing the multicellular tissue or organ culture systems. In the simplest method the organoid bodies obtained from the stem cell culture are simply cultivated further with a sufficient nutrient supply and an optional supply of special differentiation and growth factors until the desired amount and/or the desired development stage has been achieved. Alternatively, it may be advantageous to cultivate complete organic bodies of a development stage or parts of them (e.g., with desired structures) together with complete organoid bodies of another development stage or parts of them (e.g., with desired structures) and/or differentiated individual cells derived from them and/or undifferentiated adult stem cells. This could achieve, e.g., a more rapid reproduction of desired cells and/or a more rapid or more specific development of desired structures. In this instance the different organoid bodies or parts of them and/or the differentiated or undifferentiated cells preferably have the same origin.

In a preferred embodiment the tissue or organ culture system according to the invention comprises a physiologically compatible matrix or a physiologically compatible carrier system for the cells. It is especially preferable if the matrix or the carrier system can be degraded in the body. A great number of such matrices and carrier materials is known in the state of the art (see, e.g., WO 2004/7029230, WO 03/029446) and is also in part commercially available.

A few non-limiting examples of suitable materials are plastics that are compatible with the body such as nylon, polycarbonate, polytetrafluoroethylene, etc. and especially physiologically degradable synthetic polymers and biopolymers, e.g., alginate, collagen, chitin, chitosan, polylactic acid, polyglycolic acid, heparin, hyaluronic acid, polyrotaxan, gelatin, elastin, fibrin, laminin, fibronectin, etc., as well as their combinations. A special embodiment concerns sterilized acellular, that is, cell-free, biological material, e.g., small intestine submucosa (SIS) or a natural collagen- or chitin/chitosan matrix.

The matrix or the carrier system preferably has a defined form that is especially favorable for the intended use, e.g., as implant. The form can correspond, e.g., to the form of the natural tissue or organ and/or be advantageous for the preservation of a certain three-dimensional cell arrangement and/or for the supplying of the cells on or in the matrix with nutrients and/or for the integration of the implant and/or of the cells into the body. A large number of suitable forms are known in the state of the art depending on the type and function of the particular damaged tissue and/or organ and of the type of cells used. The matrix or the carrier system may be solid, semi-solid or liquid. A few non-limiting examples are matrices or carrier systems in the form of beads, including microbeads, a foam, gel, hydrocolloid, a membrane, a thread, a net, a sponge or another porous structure, a textile fabric, fleece or a natural organ or tissue.

In one embodiment the tissue or organ culture system furthermore comprises a bioadhesive. This bioadhesive can serve to improve the adhesion of the cultivated cells on the matrix or the carrier and/or to enable the connection of an implanted tissue or organ system with the tissue of a recipient. In a preferred embodiment the bioadhesive is based on fibrin and is, e.g., a fibrin adhesive. Such fibrin adhesives and equivalent bioadhesives are also commercially available.

As already mentioned above, a significant aspect of the invention consists in the use of the multicellular tissue and organ culture systems in accordance with the invention for the restoration or assumption of the function of damaged or lacking tissues or organs of an animal, preferably human, individual. The pluripotent or multipotent adult stem cells from which the organoid bodies used to produce the multicellular tissue or organ culture system arise preferably stem from the individual with a damaged or lacking tissue or organ himself. The use of such an "autologous" material can avoid the initially described problems with rejection reactions and transfers of diseases from foreign donors.

The damaged tissue or organ whose function is to be restored or assumed can basically be any organ or tissue whose specific cell types can be cultivated with the present method. A few preferred but in no way limiting examples include skin, nerve tissue, muscle tissue, connective tissue, cartilaginous tissue, neuromuscular tissue, bone tissue, glandular tissue, gastrointestinal tissue, vessels, heart, liver, kidney, lung, blood cells, etc.

The most frequent form of the use of the multicellular tissue and organ culture systems in accordance with the invention will be the use as implant.

However, other uses are also possible, especially medical uses. In a specific embodiment the multicellular tissue or organ culture system is used extracorporally in its function as tissue or organ replacement. A concrete example for this would be the use of an artificial kidney or liver system for washing blood. Other suitable uses, e.g., for the production of tissue-specific and/or organ-specific substances are readily apparent to those skilled in the art.

a,b: PGP 9.5-marked nerve cells show multipolar processes that exhibit numerous varicosities. c,d: The neurofilament system (bright arrows, marked green in the original photo) extends through the pericaryon into the cytoplasmic processes. GFAP immunoreactive glia cells (dark arrows, marked red in the original photo) are in close proximity. e,f: α-SMA-marked cells (dark arrows, red in the original) and NF-marked nerve cells (bright arrows, green in the original) form a primitive neuromuscular network (e), wherein contacts are established over considerably long distances (f). g: immunostaining of GFAP (dark arrows, red in the original) and NF (bright arrows, green in the original) in 3 weeks old OBs with concentrations of nerve- and glia cells. h: immunostaining of α-SMA (dark arrows, red in the original) and NF (bright arrows, green in the original) in 3 weeks old OBs in an advanced stage of the formation of a neuromuscular network. i, j: Cells immunoreactive for NF were found in cross sections of 8 weeks old OBs in the direct vicinity of cells that were immunoreactive for α-SMA, similarly as in native tissues. k: A subset of cells shows a positive staining for amylase (bright arrows, green in the original). l: Another cell subset contains granular vesicles having immunoreactivity for insulin. The nuclei are counterstained with DAPI (blue in the original).

Figure 3:
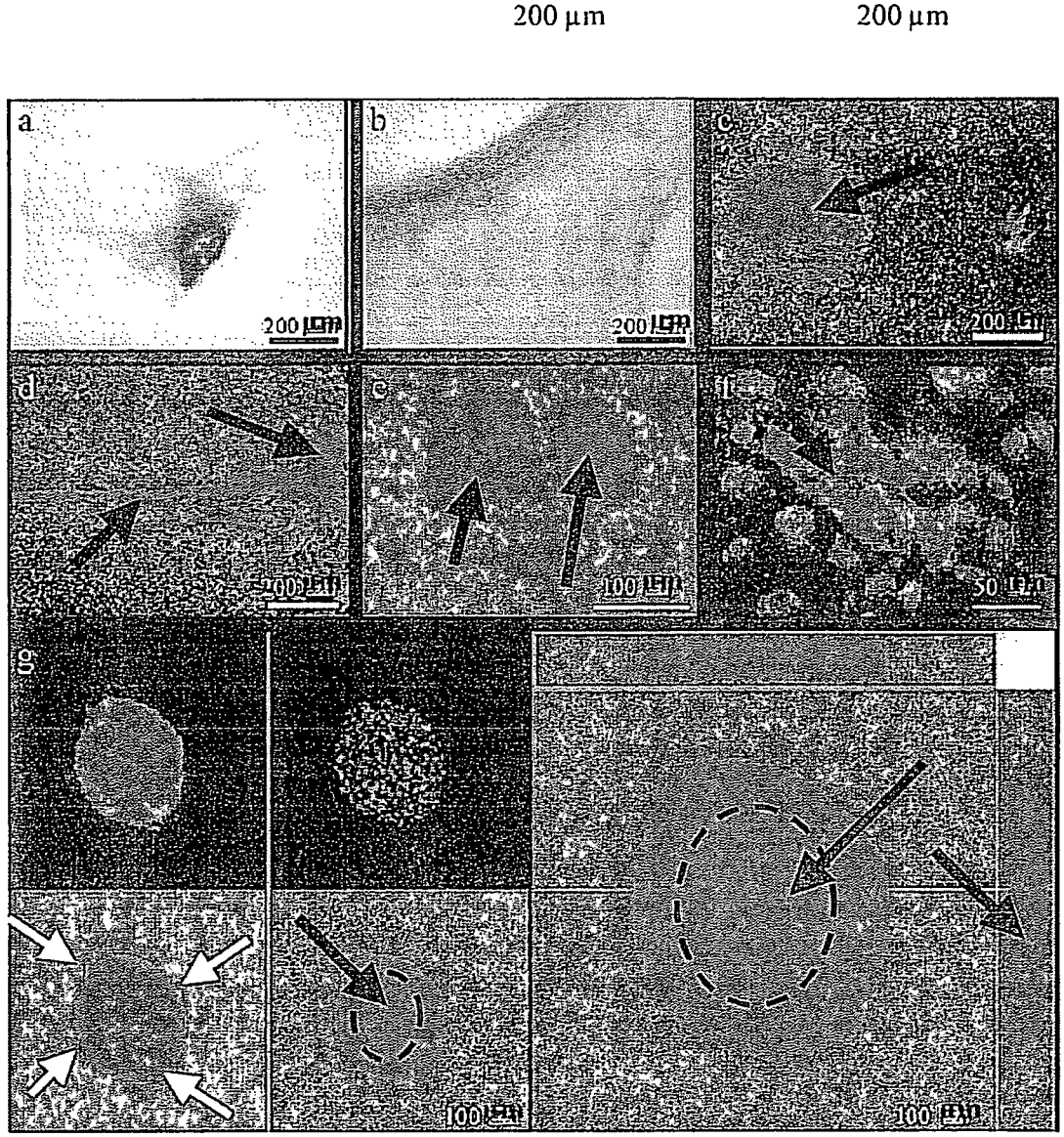

FIG. 3 shows the expression of extracellular matrix components and cytokeratins.

a,b: Globular (a) and fibrillary (b) depots of proteoglycans yielded a staining with Alcian blue. c-e: The globular (c) and fibrillary (d) areas are immunoreactive for the cartilage matrix protein collagen II. Two individual cells (e) show a cytoplasmic marking of collagen II. f: Cells that are immunoreactive are arranged in clusters. g: confocal laser scanning microscopy of an OB. The collagen II immunoreactivity (dark arrows, marked red in the original) increases toward the middle of the OB. Vigilin-immunoreactive cells (bright arrows, marked green in the original) are localized primarily on the outer edge of the OB, which indicates their high translation activity. The nuclei are counterstained with DAPI.

Figure 4:
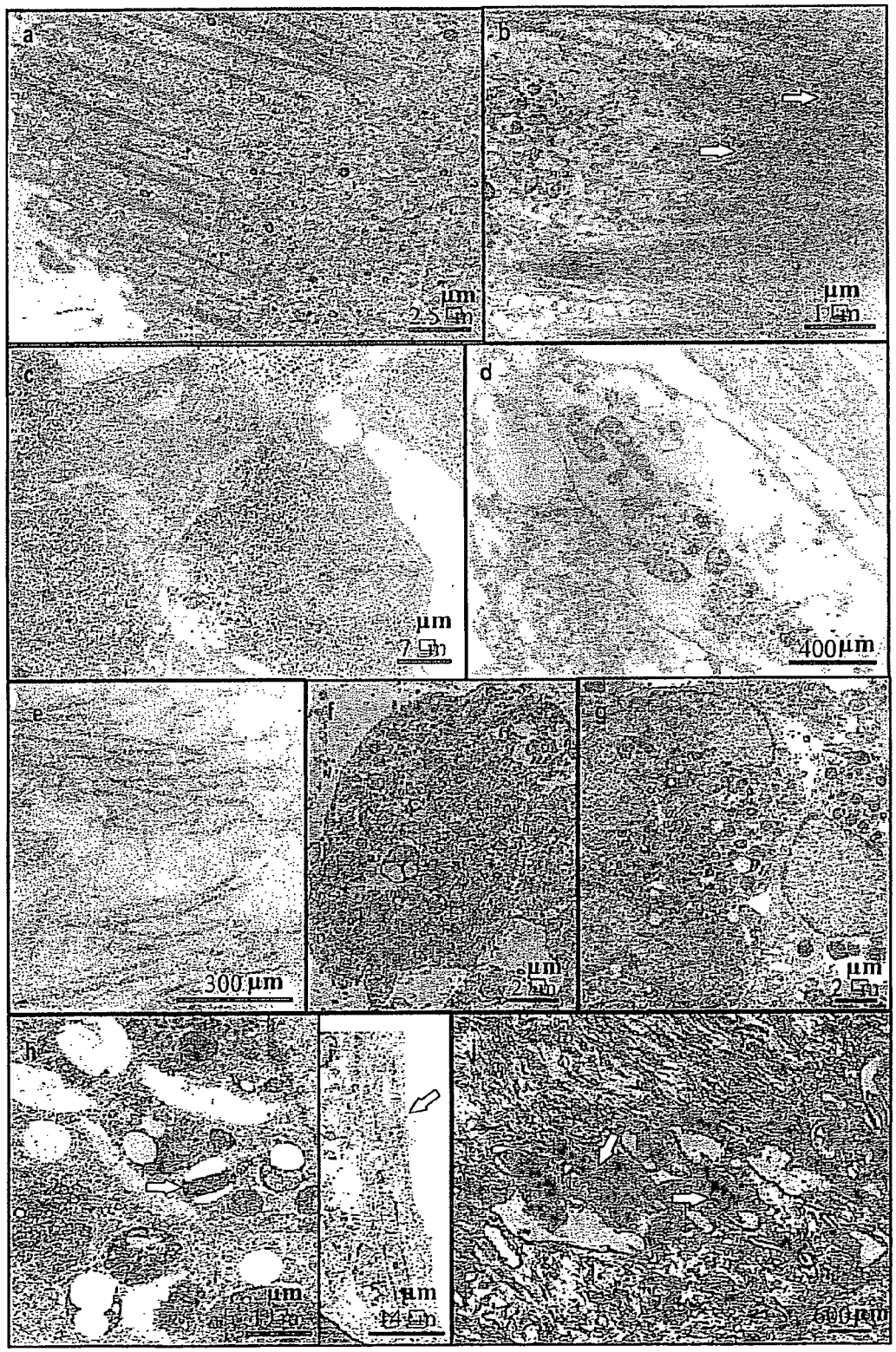

FIG. 4 shows the transmission electron microscopy of differentiated OB a-c: smooth muscle cells with myofilaments. The myofilament system extends through the cytoplasm in disseminated bundles (a) and shows typical dense bodies (arrows) (b). The myoblasts shows star-shaped cellular processes that form a connecting network (c). d: cellular processes with an accumulation of numerous small-size vesicles that most likely correspond to nerve-fiber varicosities. e: collagen and reticular fibers. f-h: Secretory cells show electrodense vesicles. f). Secretory cells frequently contact each other in order to form acinus-like structures (g). A subgroup of secretory cells contains vesicles (arrow) corresponding to ultrastructural features of endocrine granula (h), e.g., beta granula of insulin-producing cells. 1: Beginning of the formation of an epithelial surface (arrow) in eight weeks old OBs. j: typical cell contacts between keratinocytes and desmosomes (arrows).

Figure 5:
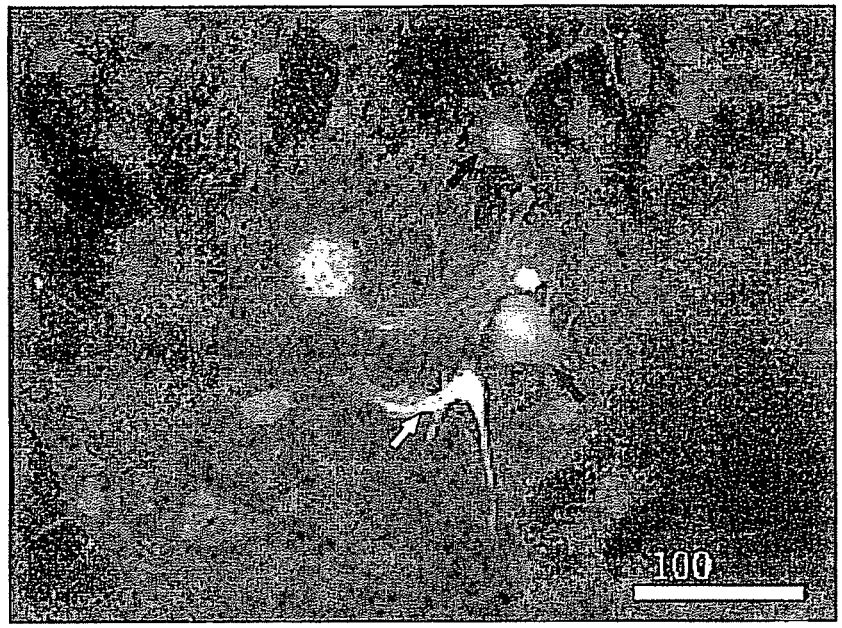
Figure 5:
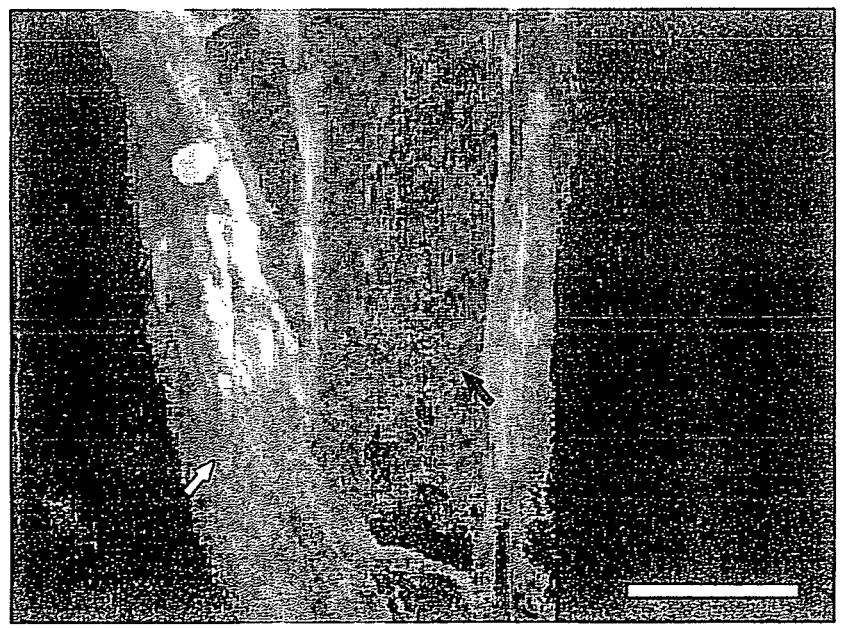

FIG. 5 shows nerve-muscle complexes from the tissue culture; bright arrows (green in the original) signify nerve cells, dark arrows (red in the original) signify muscle cells. Above: individual cells; below: longitudinal sections of three-dimensional cell complexes.

Figure 6:
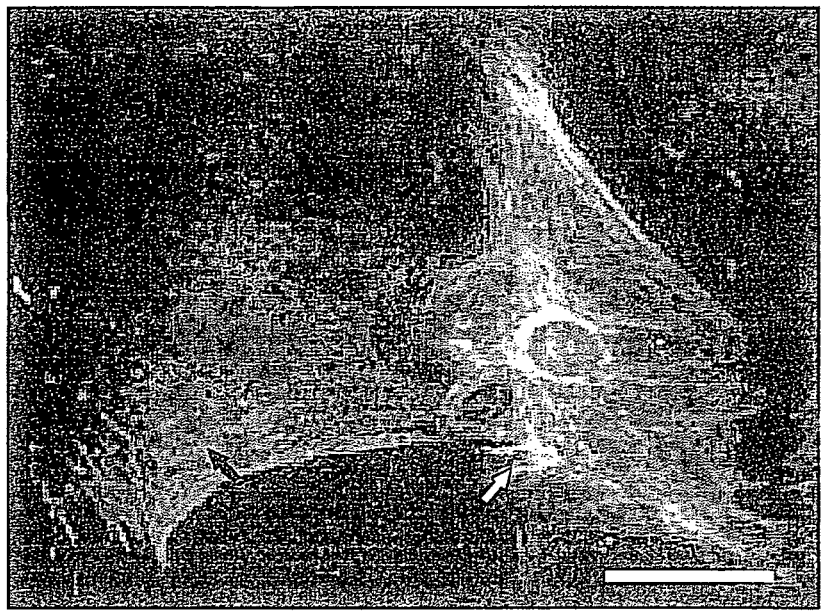
Figure 6:
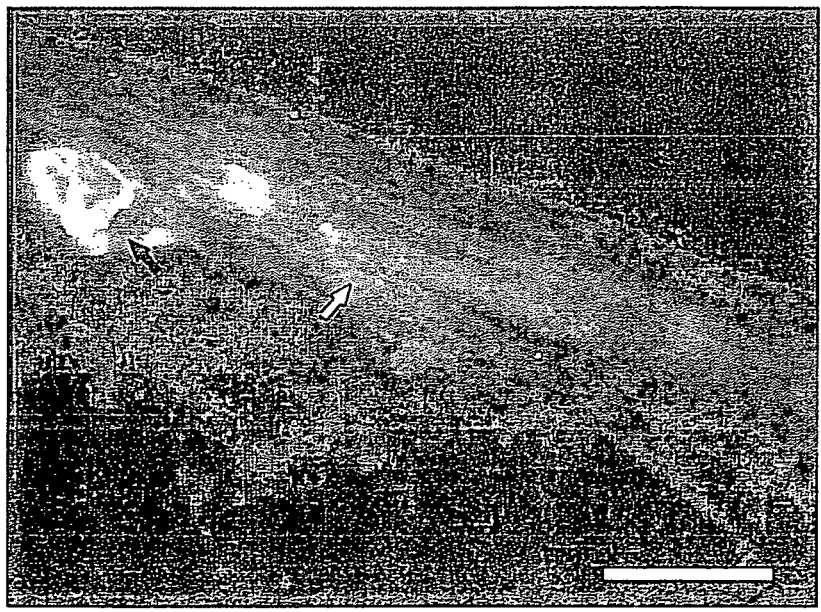

FIG. 6 shows nerve-glia complexes from the tissue culture; bright arrows (green in the original) signify nerve cells, dark arrows (red in the original) signify glia cells. Above: individual cells; below: longitudinal sections of three-dimensional cell complexes.

DETAILED DESCRIPTION OF THE INVENTION

Figure 1:
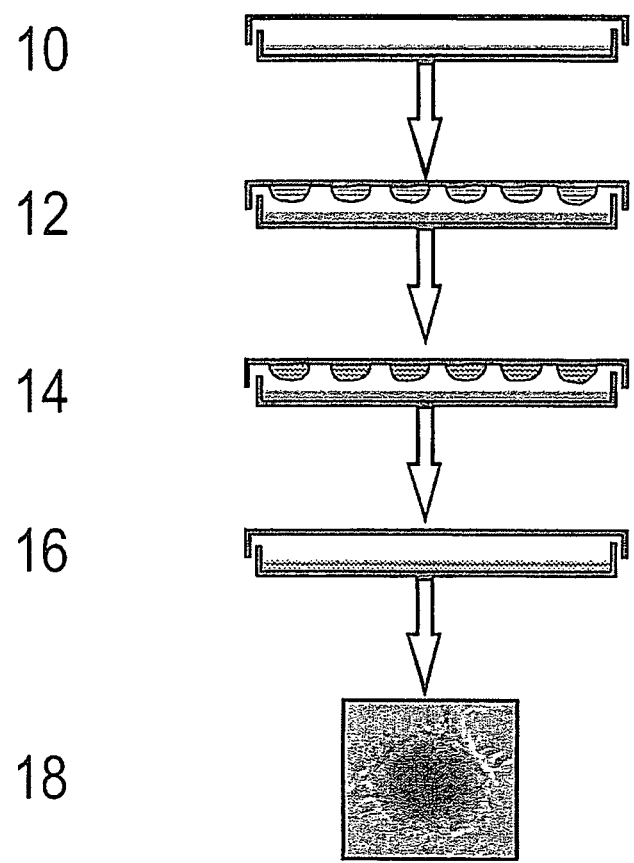
FIG. 1 schematically shows the cultivation of the stem cells in surface culture and in hanging drops as well as the formation and further cultivation of organoid bodies.

According to the scheme shown in FIG. 1, in order to obtain the stem cells exocrine glandular tissue, e.g., acinar tissue, preferably from a salivary gland or the pancreas, is taken into culture mechanically and enzymatically comminuted (step 10 in FIG. 1). In contrast to the indications of Bachem et al., Gastroenterol. 115:421-432 (1998), and Grosfils et al., Res. Comm. Chem. Pathol. Pharmacol. 79:99-115 (1993), no tissue blocks are cultivated from which cells are to grow out, but rather the tissue is more strongly comminuted under the condition that the cell aggregates of the acini remain intact to a very large extent.

These cells and cell aggregates are cultivated in culture vessels for several weeks. Every 2 to 3 days the medium is changed, during which all differentiated cells are removed. The cells persisting in culture are undifferentiated cells with unlimited capacity to divide.

Similar cells have been isolated under the same conditions from the pancreas and described and referred to as a type of myofibroblasts or pancreatic astrocytes (Bachem et al., 1998). However, in contrast to the cells of the present invention an unlimited capacity to divide could not be observed. Furthermore, these cells could also not be passaged in an unlimited manner without losing vitality.

In a second step (12) approximately 900 to 800 cells are cultivated in 20 μl medium each in hanging drops. To this end, the drops are placed on the cover of bacteriological Petri dishes, turned over and placed over the Petri dish filled with medium so that the drops hang downward.

As a result of this type of cultivation the cell aggregates (14) referred to as organoid bodies form within 48 h, which cell aggregates are transferred into a suspension culture for approximately 6 days (16). The partial view (18) in FIG. 1 shows a micrograph of such an organoid body.

The organoid bodies growing in suspension culture form new organoid bodies that also induce the formation of new organoid bodies in individual cells. The cells can be frozen as organoid bodies as well as individual cells and retain their vitality and their differentiation potential.

Figure 2:
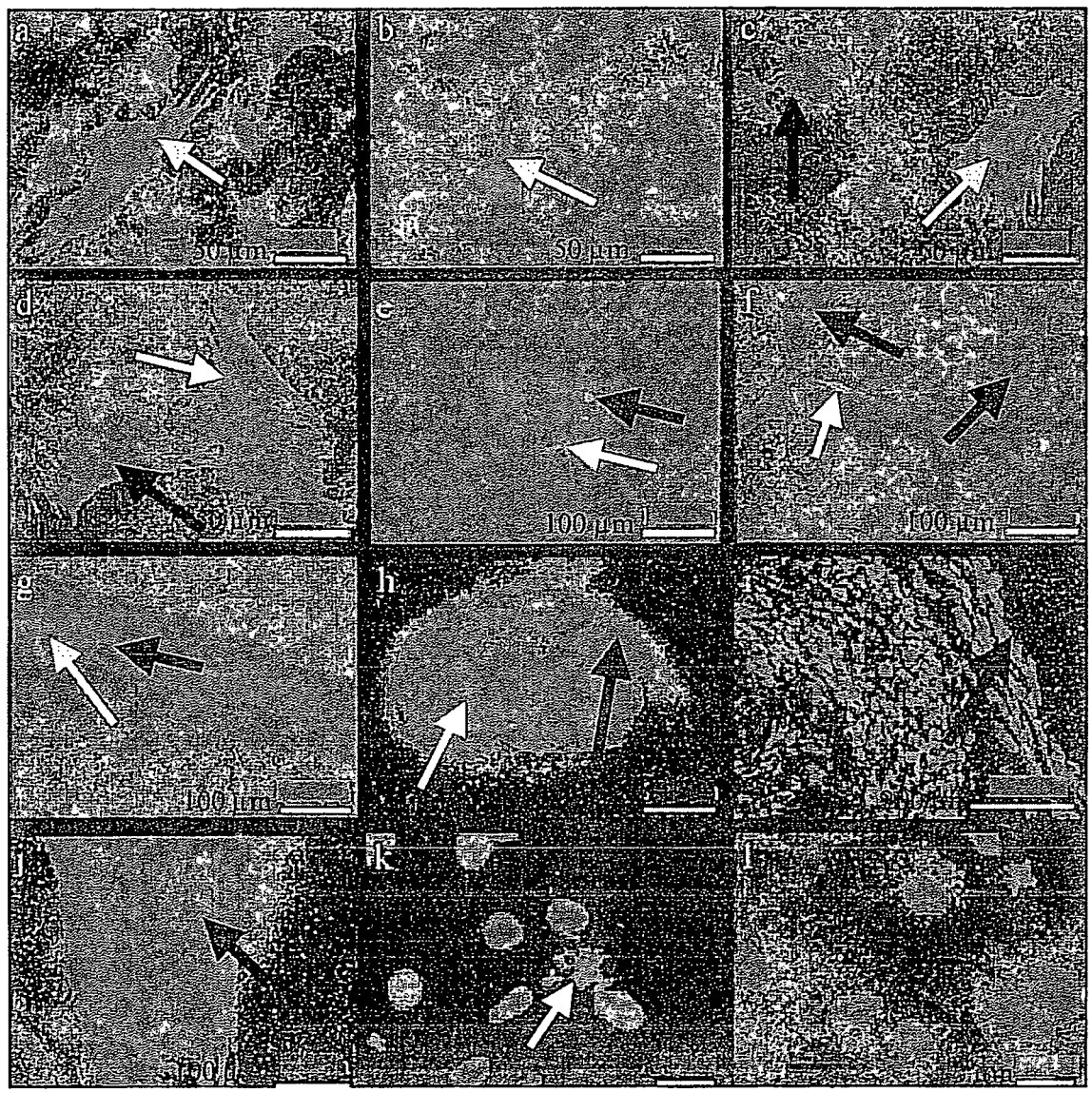
FIG. 2 shows the expression of markers of neuronal cells, glial cells and smooth muscle cells as well as of amylase and insulin in the differentiated cells of the organoid bodies.

FIGS. 2-4 show micrographs and electron micrographs of differentiated cells obtained from such organoid bodies.

It was possible to thereby observe, for example, the formation of a neuromuscular network:

Cells obtained from OBs strongly expressed (α-SMA (smooth-muscle actin) (FIGS. 2e-f). The presence of distributed bundles of myofilaments that extended through the cytoplasm was confirmed by electron microscopy (FIGS. 4a-c). Furthermore, cells were identified that were immunoreactive for the pan-neuron marker PGP 9.5 and for neurofilaments (NF). The neurofilament system extended from the pericaryon into the radial cytoplasmic processes (FIGS. 2c, d). PGP 9.5-immunoreactive cells showed numerous varicosities along their branched processes (FIGS. 2a, b, 4d) and thus resembled typical morphological features of autonomous nerve fibers. Cells that were immunoreactive for GFAP (glial fibrillary acidic protein) were in close proximity to cells that expressed neuronal markers (FIGS. 2c, d). The filamentary proteins frequently did not extend through the entire cytoplasm but rather were limited to areas adjacent to the nerve cells. Furthermore, smooth muscle cells and nerve cells were not randomly scattered but rather formed adherent networks with connections that were easily discernible (FIGS. 2e, f). Nerve fiber processes extended over considerably large distances in order to contact adjacent smooth muscle cells as their presumed targets. Thus, the two cell types showed features of a primitive neuromuscular network based on their topographical arrangement. An incipient formation of tissue-like-structures was observed in 3 weeks old OBs (FIGS. 2g-j). Here, a cluster of fibrous nerve cells was found in contact with glia cells (FIG. 2g) or was further developed to a three-dimensional neuromuscular network (FIG. 2h), which was confirmed in cross sections of 8 weeks old OBs (FIGS. 2i-j).

Detection of the expression of exocrine and endocrine pancreatic proteins:

Immunohistochemical stainings showed that cellular subsets were positive for amylase (FIG. 2k). The immunoreactive signal was limited to clearly distinguishable vesicles within the apical cytoplasm. In addition, most of the cell clusters that were immunoreactive for amylase were arranged in circles and the secretory vesicles had a position facing toward the middle, which is a morphological arrangement similar to that of exocrine pancreatic acini. Other cellular subsets showed immunoreactivity for insulin (FIG. 2l). Similarly to the amylase-positive cell clusters, the secretory product was stored in vesicular structures that were concentrated on a cell pole. The presence of secretory cells was confirmed by electron microscopy, which revealed densely distributed electrodense particles like those characteristic for excretory or incretory functions (FIGS. 4f-h).

A differentiation into chondrogenic cells and epithelial cells was also observed:

After a growth period of two months OBs exhibited chondrogenic properties. An Alcian blue staining revealed areas with high concentrations of proteoglycans (chondroitin sulfate), that occurred either as globular (FIG. 3a) or fibrillary (FIG. 3b) deposits. Immunohistochemical stainings with antibodies directed against the cartilage matrix protein collagen II additionally proved the chondrogenic activity within these globular (FIG. 3c) and fibrillary (FIG. 3d) areas. The immunoreactivity was highest in the middle of the cellular aggregates, which most likely corresponded to areas of developing extracellular cartilage matrix. This observation was confirmed by confocal microscopy (FIG. 3g): whereas the amount of collagen depots increased toward the middle of the cellular aggregates, the border areas were characterized by actively translating cells as demonstrated by their high expression of vigilin, which is usually found in cells having an active translation machinery, e.g., collagen synthesizing chondrocytes or in fibroblasts during chondroinduction. Typical individual collagen II translating chondrocytes were also observed in outgrowing cells of OBs that produced a collagen II-containing matrix that surrounded the individual cells (FIG. 3e). An ultrastructure examination of these areas was able to clearly show a network of reticular fibers and collagen fibers, the latter being identified by their characteristic band pattern (FIG. 4e). In addition to mesenchymal markers, some cells also expressed several cytokeratins, which indicates their potential for differentiation in epithelial cells. However, cells that were immunoreactive for cytokeratins were found less frequently than cells that expressed the markers of smooth muscle cells and neurons. They were typically arranged in clusters disseminated within the OBs (FIG. 3f). Typical cell contacts between keratinocytes were found by electron microscopic examinations (FIG. 4j) and in 8 weeks old OBs epithelial cells were found on the surface which grew out of the cell culture medium into the air.

On the whole, e.g. the following markers for specific cells could be tested positive so far: PGP 9.5 and NF for nerve cells, S 100 and GFAP for glia cells, SMA for muscle cells (or myofibroblasts), collagen type II for cartilage cells, amylase and trypsin for exocrine glandular cells, insulin for endocrine glandular cells, vigilin for strongly translating cells and cytokeratin for epidermal cells. In addition to the light microscopic examinations, different cell types could be characterized morphologically by electron microscopy also and cell-cell contacts were found as a sign for cellular interactions.

So far, i.a. smooth muscle cells, neurons, glia cells, epithelial cells, fat cells, cardiac cells, kidney cells, fibroblasts (e.g., skin and tendon fibroblasts), chondrocytes, endocrine and exocrine glandular cells and thus cell types of all three germ layers in these organoid bodies have been detected morphologically/histologically and/or immunochemically.

The present invention will be explained in greater detail in the following non-limiting examples.

The general working instructions customary for methods for cultivating mammalian cells, in particular human cells, are to be observed. A sterile environment in which the method is to be carried out is to be observed in any case, even if no further description for this is given. The following buffers and media were used:

| | |
|---|---|
| HEPES stock solution (pH 7.6) | 2.383 g HEPES per 100 ml A. bidest. |
| HEPES Eagle's Medium (pH 7.4) | 90 ml modified Eagle's Medium (MEM) 10 ml HEPES stock solution |
| Isolation medium (pH 7.4) | 32 ml HEPES Eagle's Medium 8 ml 5% BSA in A. bidest. 300 µl 0.1 M CaCl$_2$ 100 µl trasylol (200,000 KIU) |
| Digestion medium (pH 7.4) | 20 ml isolation medium 4 ml collagenase (collagenase NB 8 from Serva) |
| Incubation medium | Dulbecco's modified Eagle's Medium (DMEM) |
| Nutrient medium | Dulbecco's modified Eagle's Medium (DMEM) DMEM + 4500 mg/l glucose + L-glutamine – pyruvate + 20% FCS (inactivated) + 1 ml/100 ml pen/strep (10000 U/10000 µg/ml) or DMEM + 10% autoplasma + 1 ml/100 ml pen/strep, warm to 37° C. before use |
| Differentiation medium | 380 ml DMEM 95 ml 30 min at 54° C. inactivated FCS 5 ml glutamine (GIBCO BRL) 5 ml (3,5 µl β-mercaptoethanol per 5 ml PBS) 5 ml nonessential amino acids (GIBCO BRL) 5 ml penicillin/streptomycin (GIBCO BRL) (10000 U/10000 µg/ml) |

Instead of fetal calf serum (FCS) in the nutrient medium and differentiation medium plasma or serum of another suitable species, e.g., human plasma, or less preferably, human serum, may optionally also be used. It is preferable to use auto-plasma or, less preferably, autoserum of the animal or human tissue donor. This is especially significant if the tissue donor is identical with the later recipient of the stem cells or of differentiated cells derived from them. Such an autologous treatment is preferred for preventing any rejection reaction.

Instead of the DMEM medium used, the nutrient medium may also contain another suitable base medium known for the cultivation of eukaryotic cells, especially mammalian cells, as base medium in which the differentiated cells die and the desired stem cells proliferate. The isolation medium, incubation medium and differentiation medium may also contain a different customary and suitable base medium.

The following examples 1 to 3 describe working protocols for isolating and cultivating adult pluripotent stem cells from acinar tissue of the pancreas or from acinar and tubular tissue of the salivary gland.

EXAMPLE 1

In order to isolate and cultivate human adult stem cells human tissue was obtained from adult patients immediately after a surgical intervention and prepared at once. Healthy tissue was separated from the surgically removed tissue, e.g., pancreatic tissue, and taken up (at 20° C., lesser metabolism) in digestion medium containing HEPES Eagle's medium (pH 7.4), 0.1 mM HEPES buffer (pH, 7.6), 70% (vol./vol.) modified Eagle's medium, 0.5% (vol./vol.) trasylol (Bayer AG, Leverkusen, Germany), 1% (wt./vol.) bovine serum albumin), 2.4 mM CaCl$_2$ and collagenase (0.63 P/mg, Serva, Heidelberg, Germany). The pancreatic tissue was very finely comminuted with shears, fatty tissue floating on top removed by suction and the tissue suspension gassed with Carbogen (Messer, Krefeld, Germany) without the nozzle entering into the medium with the cells (reduction of mechanical stress) and adjusted therewith to pH 7.4. The suspension was then incubated in a 25 ml Erlenmeyer flask (covered with aluminum foil) under constant agitation (150-200 cycles per minute) at 37° C. in 10 ml digestion medium. After 15-20 minutes the fat floating on top and the medium were removed by suction and the tissue was again comminuted and rinsed with medium without collagenase (repeat procedure at least twice, preferably until cell fraction transparent), whereupon digestion medium was added and another gassing was performed for approximately 1 minute with Carbogen. A digestion with collagenase followed again for 15 minutes at 37° C. in an agitator using the same buffer. After the digestion the acini were dissociated by successively drawing them up and ejecting through 10 ml, 5 ml and 2 ml glass pipettes with narrow openings and filtered through a single-layer nylon mesh (Polymon PES-200/45, Angst & Pfister AG, Zurich, Switzerland) with a mesh size of approximately 250 µm. The acini were centrifuged (at 37° C. and 600-800 rpm in a Beckman GPR centrifuge, corresponds to approximately 50-100 g) and further purified by being washed in incubation medium containing 24.5 mM HEPES (pH 7.5), 96 mM NaCl, 6 mM KCl, 1 mM $MgCl_2$, 2.5 mM $NaH_2PO_4$, 0. mM $CaCl_2$, 11.5 mM glucose, 5 mM sodium pyruvate, 5 mM sodium glutamate, 5 mM sodium fumarate, 1% (vol./vol.) modified Eagle's Medium, 1% (wt./vol.) bovine serum albumin, equilibrated with Carbogen and adjusted to pH 7.4. The washing procedure (centrifugation, removal by suction, re-suspension) was repeated five times. Unless otherwise indicated, the work was performed at approximately 20° C. in the above isolation.

The acini were re-suspended in incubation medium and cultivated at 37° C. in a humid atmosphere with 5% $CO_2$. The acinar tissue died rapidly (within two days) and the dying differentiated cells separated from the adjacent cells without damaging them (gentle isolation) and the stem cells that were not dying sank to the bottom, to which they adhered. The differentiated acini cells are not capable of doing this. The incubation medium was replaced for the first time on the second or third day after the seeding, during which a large part of the freely floating acini and acinar cells was removed. At this time the first stem cells or their precursors had attached to the bottom and began to divide. The medium replacement was repeated thereafter on every third day and differentiated acinar pancreatic cells were removed at each medium replacement.

On the seventh day in culture the cells were passaged with a solution consisting of 2 ml PBS, 1 ml trypsin (+0.05% EDTA) and 2 ml incubation medium, during which the cells separated from the bottom of the culture dish. The cell suspension was centrifuged 5 minutes at approximately 1000 rpm (Beckmann GPR centrifuge), the supernatant removed by suction and the cells re-suspended in 2 ml incubation medium and transferred to a medium-sized cell culture bottle to which 10 ml incubation medium were added.

On the fourteenth day in culture the cells were passaged again but this time with 6 ml PBS, 3 ml trypsin/EDTA and 6 ml incubation medium. The cell suspension was centrifuged for 5 minutes at 1000 rpm, the supernatant removed by suction and the cells were re-suspended in 6 ml incubation medium, transferred to 3 medium cell culture bottles and 10 ml incubation medium added to each one.

On day 17 a third passage took place to a total of 6 medium cell culture bottles and on day 24 a fourth passage to a total of 12 medium cell culture bottles. Now at the latest all primary cells except for the stem cells had been removed from the cell culture.

The stem cells may be cultivated further and passaged and seeded as often as desired. The seeding preferably takes place at a density of $2-4\times10^5$ cells/$cm^2$ in the incubation medium.

EXAMPLE 2

Pancreatic acini were obtained from male Sprague-Dawley rats (20-300 g) that had been narcotized ($CO_2$) and exsanguinated via the dorsal aorta. A cannula was introduced transduodenally into the pancreatic duct and 10 ml digestion medium that contained HEPES Eagle's medium (pH 7.4), 0.1 mM HEPES buffer (pH, 7.6), 70% (vol./vol.) Modified Eagle's medium, 0.5% (vol./vol.) trasylol (Bayer AG, Leverkusen, Germany), 1% (wt./vol.) bovine serum albumin, 2.4 mM $CaCl_2$ and collagenase (0.63 P/mg, Serva, Heidelberg, Germany) was injected into the pancreas from the rear. Prior to the removal the pancreas had been partially freed of the adhering fatty tissue, lymph nodes and blood vessels. Then, fresh pancreatic tissue was taken into digestion medium (at 20° C., lesser metabolism) and the pancreatic tissue very finely comminuted with shears and processed as described in example 1.

EXAMPLE 3

The isolation and cultivation from exocrine tissue of the parotid gland took place analogously to the pancreas protocol with the following deviations:
1. The exocrine tissue of the parotid gland was a mixture of acinar tissue and tubular tissue.
2. Since salivary glands contain less proteases and amylases than the pancreas, it is possible to store salivary gland tissue for a while in a refrigerator at approximately 4° C. without damaging the tissue too much. In the concrete exemplary case the storage time was 15 h and entailed no disadvantageous consequences for the isolation of the desired stem cells.

If the stem cells produced as described above from exocrine glandular tissue are to be used directly or indirectly (production of organoid bodies and/or differentiated cells from them) for human therapeutic purposes, various conditions also have to be met for safety reasons in order to rule out the possibility of a risk to the patient to be treated, in particular:

the use of human serum, preferably autoplasma of the patient instead of FCS, if necessary, purification of the serum or plasma exclusion of any animal source from further media additives highest purity of all substances, sterility of equipment and environment sterility and purity of the stem cell culture by multiple passaging of the stem cells and monitoring for contamination by mycoplasmas or other microorganisms careful checking of the source tissue and of the stem cells for tumorgenicity.

The following examples 4 and 5 describe in detail two working protocol for producing organoid bodies and differentiated cells.

EXAMPLE 4

The undifferentiated cells are trypsinated with a solution of 10 ml PBS, 4 ml trypsin, 8 ml differentiation medium and centrifuged off for 5 minutes. The resulting pellet is re-suspended in differentiation medium in such a manner that a dilution of 3000 cells per 100 µl medium is established. The cells are subsequently well suspended again with a 3 ml pipette.

The cover is removed from bacteriological Petri dishes that had previously been coated with 15 ml PBS (37° C.) per plate, and inverted. Approximately fifty 20 ml drops are placed with the aid of an automatic pipette on a cover. The cover is then rapidly inverted and placed on the Petri dish filled with differentiation medium so that the drops hang downward. The Petri dishes are subsequently carefully placed in an incubator and incubated for 48 h.

Then, the cells that are aggregated in the hanging drops, which cells are to be referred to as organoid bodies (OB) here, are transferred from four covers at a time into one bacteriological Petri dish each with 5 ml incubation medium with 20% FCS and cultivated for another 96 h.

The organoid bodies are now carefully collected with a pipette and transferred into cell culture vessels coated with 0.1% gelatin and containing differentiation medium. In an especially preferred embodiment of the method 6 cm Petri dishes coated with 0.1% gelatin into which 4 ml differentiation medium had been placed and that were subsequently each loaded with 6 organoid bodies are used as culture vessel. Another preferred culture vessel are chamber slides coated with 0.1% gelatin into which 3 ml differentiation medium had been placed and that were subsequently each loaded with 3-8 organoid bodies. In addition, 24-well microtiter plates can also be used that were coated with 0.1% gelatin and into which 1.5 ml differentiation medium had been placed per well and that are subsequently coated with 4 organoid bodies each.

Cultivated in this manner, the differentiation capacity of the cells in the organoid bodies is activated and the cells differentiate into cells of the three germ layers, mesoderm, entoderm and ectoderm. The cells may be stored and cultivated both as organoid bodies as well as individual cells and retain their pluripotency.

EXAMPLE 5

Stem cells after the 42nd day of cultivation were preferably used for the induction of the differentiation. The use of stem cells after the 3rd or 4th passage or of cells that had been stored at the temperature of liquid nitrogen for 12-18 months was also possible without problems.

At first, the cells were transferred into differentiation medium with the composition indicated above and adjusted to a density of approximately $3 \times 10^4$ cells/ml, e.g., by trypsin treatment of a stem cell culture in nutrient medium, 5-minute centrifugation at 1000 rpm and re-suspension of the pellet in differentiation medium and dilution to the extent required.

Subsequently, approximately 50 20-µl drops (600 cells/20 µl) were placed on the inside of the cover of a bacteriological Petri dish (plugged tips) and the cover carefully inverted onto the Petri dishes filled with PBS so that the drops hung downward. A new tip was used for each cover. The Petri dishes were subsequently carefully placed into the incubator and incubated for 48 h at 37° C.

Then, the aggregated cells in the hanging drops, the organoid bodies (OB), were transferred from four covers at a time into one bacteriological Petri dish each with 5 ml incubation medium with 20% FCS (hold cover obliquely and rinse the OBs off with approximately 2.5 ml nutrient medium) and cultivated for another 5-9 days, preferably 96 h.

The organoid bodies were now carefully collected with a pipette and transferred into cell culture vessels coated with 0.1% gelatin and containing differentiation medium. The organoid bodies now proliferated and grew in partially individual cell colonies that were able to be proliferated, isolated and proliferated again. In an especially preferred embodiment of the method 6 cm Petri dishes coated with 0.1% gelatin were used as culture vessels into which 4 ml differentiation medium had been placed and they were each loaded with 6 organoid bodies. Another preferred culture vessel was chamber slides coated with 0.1% gelatin into which 3 ml differentiation medium had been placed and that were each subsequently loaded with 3-8 organoid bodies, and Thermanox plates (Nalge Nonc International, USA) for electron micrographic studies. Another alternative was 24-well microtiter plates coated with 0.1% gelatin into each of which 1.5 ml differentiation medium per well had been placed and that were subsequently each loaded with 4 organoid bodies.

In a preferred embodiment of the method, OBs were cultivated approximately 7 weeks in the gelatin-coated 6 cm Petri dishes and thereafter individual organoid bodies were cut out using the Microdissector (Eppendorf, Hamburg, Germany) according to the instructions of the manufacturer and then transferred, e.g., onto fresh 6 cm Petri dishes, chamber slides or Thermanox plates. In a further preferred embodiment individual OBs were separated with pipette tips by gentle suction and transferred, followed by, e.g., observation under an inverse microscope.

EXAMPLE 6

Characterization of Differentiated Cells in the Organoid Bodies

1. Immunohistochemistry

Organoid bodies, that had been cultivated at least 3 weeks on chamber slides, as well as cross sections of "long-term" OBs were rinsed twice in PBS, fixed for five minutes with methanol:acetone (7:3) containing 1 g/ml DAPI (Roche, Switzerland) at $-20°$ C. and washed three times in PBS. After incubation in 10% normal goat serum at room temperature for 15 minutes, the samples were incubated overnight with primary antibodies at 4° C. in a humidification chamber. The primary antibodies were directed against the protein gene product 9.5 (PGP 9.5, polyclonal rabbit antibody, 1:400, Ultraclone, Isle of Wight), neurofilaments (NF-Pan-Cocktail, polyclonal rabbit antibody, 1:200, Biotrend, Germany), $\alpha$-smooth muscle actin ($\alpha$-SMA, monoclonal mouse antibody, 1:100, DAKO, Denmark), glial fibrillary acidic protein (GFAP, monoclonal mouse antibody, 1:100, DAKO, Denmark), collagen II (monoclonal mouse antibody, II-II-6B3, 1:20, Developmental Studies Hybridoma Bank, University of Iowa, USA), vigilin FP3 (1:200, Kügler et al., 1996), cytokeratins (Pan Cytokeratin, monoclonal mouse antibody, 1:100, Sigma, USA), alpha-amylase (polyclonal rabbit antibody, 1:100, Calbiochem, Germany) and insulin (monoclonal mouse antibody, 0.5 g/ml, Dianova, Germany). After having been rinsed three times with PBS, slides were incubated for 45 minutes at 37° C. with either Cy3-marked anti-mouse IgG or FITC-marked anti-rabbit IgG (Dianova), each diluted 1:200. The slides were washed three times in PBS, coated with Vectashield Mounting Medium (Vector, USA) and analyzed with a fluorescence microscope (Axiosop Zeiss, Germany) or with a confocal laser scanning microscope (LSM 510 Zeiss, Germany). An Alcian blue staining was performed with standard methods.

2. Transmission Electron Microscopy

OBs were cultivated for at least 3 weeks on Thermanox plates (Nalge Nonc International, USA). Samples adhering to the Thermanox were incubated at pH 7.4 for 24 h by being immersed in 0.1 M cacodylate buffer containing 2.5% glutaraldehyde and 2% paraformaldehyde. After a post-fixing in 1% $OsO_4$, "en bloc" staining with 2% uranylacetate and dehydration in pure alcohols the samples were embedded in Araldite. After removal of the Thermanox plate, semithin cuts were performed either tangentially or vertically to the embedded cell culture and stained with methylene blue and azure II. Ultrathin sections were stained out of the regions of interest, stained with lead citrate and examined using a transmission electron microscope (Phillips, EM 109).

EXAMPLE 7

Organoid bodies were produced as described above and allowed to grow in differentiation medium without additional differentiation factors (approximately 2-4 weeks) until neuromuscular networks could be observed. FIG. 5 shows such nerve-muscle complexes from the tissue culture as individual cells and as longitudinal sections of these three-dimensional cell complexes. These nerve-muscle complexes can be further developed in the organoid bodies or removed from the organoid bodies and cultivated further and developed separately. The further cultivation may be carried out in a traditional culture vessel or already in a carrier system or a matrix as described above, preferably on a collagen basis. The latter method facilitates a later implantation of the tissue or organ culture systems.

EXAMPLE 8

Organoid bodies were produced as described above and allowed to grow in differentiation medium without additional differentiation factors (approximately 2-4 weeks) until nerve-glia complexes could be observed. FIG. 6 shows such nerve-glia complexes from the tissue culture as individual cells and as longitudinal sections of these three-dimensional cell complexes. These nerve-glia complexes can be further developed in the organoid bodies or removed from the organoid bodies and cultivated further and developed separately. The further cultivation may be carried out in a traditional culture vessel or already in a carrier system or a matrix as described above, preferably on a collagen basis. The latter method facilitates a later implantation of the issue or organ culture systems.

The features of the invention disclosed in the previous description, the claims and the drawings may be significant individually as well as in combination for the realization of the invention in its different embodiments.

The invention claimed is:

1. A method of producing a three-dimensional multicellular tissue or organ comprising:
(a) culturing mammalian digests of acinary pancreatic tissue, acinary salivary gland tissue or exocrine sweat gland tissue in a medium to obtain acinary tissue cell aggregates or exocrine sweat gland tissue cell aggregates,
(b) culturing the acinary tissue cell aggregates or exocrine sweat gland tissue cell aggregates obtained in step (a) in tissue vessels such that acinary tissue stem cells or exocrine sweat gland tissue stem cells adhere to said vessel,
(c) cultivating the stem cells obtained from step (b) in medium in hanging drops, thereby forming organoid bodies comprising three-dimensional multicellular mammalian cell aggregates, wherein said organoid bodies contain cells of all three germ layers, and
(d) cultivating the organoid bodies formed from step (c) on a physiologically compatible matrix coated tissue carrier in medium comprising differentiation factors and/or growth factors or in co-culture with differentiated cells or tissue pieces of the desired target tissue to obtain a desired tissue.

2. The method according to claim 1, wherein the mammalian digests are human digests.

3. The method according to claim 1, wherein the cells of the organoid bodies are selected from the group consisting of osteoblasts, osteoclasts, chondrocytes, adipocytes, fibroblasts, muscle cells, endothelial cells, epithelial cells, hematopoietic cells, sensory cells, endocrine and exocrine glandular cells, glia cells, neuronal cells, oligodendrocytes, blood cells, intestinal cells, cardiac cells, lung cells, liver cells, kidney cells and pancreatic cells.

4. The method according to claim 1, wherein a cell composition of the organoid bodies is determined by cultivating the organoid bodies with cell-type specific differentiation and/or growth factors in a medium.

5. The method according to claim 4, wherein the growth and/or differentiation factors are selected from the group consisting of bFGF, VEGF, DMSO and isoproterenol, fibroblast growth factor 4 (FGF4), hepatocyte growth factor (HGF), TGF beta 1, EGF, KGF, retinoic acid, beta NFG, BMP 4 and activin A.

6. The method according to claim 1, wherein at least two different cell types of the organoid bodies form tissue or organ structures.

7. The method according to claim 6, wherein said at least two different cell types of the organoid bodies form neuromuscular structures or glia-nerve cell structures or skin cell structures.

8. The method according to claim 6, further comprising:
removing said tissue or organ structures from the organoid bodies; and cultivating said tissue or organ structures under suitable conditions for maintaining and/or developing the structures.

9. The method according to claim 8, comprising further cultivating said structures until a desired cell amount or development stage has been attained.

10. The method according to claim 8, wherein removing the tissue or organ structures from the organoid bodies is aided by a slow micromanipulation technique.

11. The method according to claim 1, further comprising cultivating at least a portion of a complete organoid bodies of a first development stage together with at least one organoid body selected from the group consisting of at least a portion of complete organoid bodies of a second development stage, differentiated individual cells derived from said organoid bodies of said second development stage and undifferentiated adult stem cells.

12. The method according to claim 11, wherein said portions of the organoid bodies include tissue and organ structures.

13. The method according to claim 1, wherein the matrix coated tissue carrier system is degradable in the body.

14. The method according to claim 13, wherein the matrix coated tissue carrier system comprises at least one of the acellular materials selected from the group consisting of small intestinal submucosa (SIS), alginate, collagen, chitin, chitosan, polylactic acid, polyglycolic acid, heparin, hyaluronic acid, polyrotaxan, gelatin, elastin, fibrin, laminin, and fibronectin.

15. The method according to claim 1, wherein the matrix coated tissue carrier system has a defined form.

16. The method according to claim 15, wherein the matrix coated tissue carrier system has a form selected from the group consisting of beads, microbeads, a foam, gel, hydrocolloid, a membrane, a thread, a net, a sponge, a porous structure, a textile fabric, fleece, a natural organ, and tissue.

17. The method according to claim 1, wherein the tissue or organ further comprises a bioadhesive.

18. The method according to claim 17, wherein the bioadhesive is based on fibrin.

19. The method according to claim 18, wherein the bioadhesive is a fibrin adhesive.

* * * * *